(12) United States Patent
Clegg et al.

(10) Patent No.: US 8,390,813 B2
(45) Date of Patent: Mar. 5, 2013

(54) APPARATUS AND METHOD FOR MONITORING OF GAS HAVING STABLE ISOTOPES

(75) Inventors: Samuel M Clegg, Los Alamos, NM (US); Julianna E Fessenden-Rahn, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 340 days.

(21) Appl. No.: 12/429,364

(22) Filed: Apr. 24, 2009

(65) Prior Publication Data

US 2009/0273781 A1   Nov. 5, 2009

Related U.S. Application Data

(60) Provisional application No. 61/126,299, filed on May 2, 2008.

(51) Int. Cl.
*G01N 21/00* (2006.01)

(52) U.S. Cl. ........ 356/437; 356/409; 356/317; 250/433; 250/435; 250/339.1; 250/338.5; 250/343

(58) Field of Classification Search .......... 356/440, 356/437, 632; 250/346, 350, 351, 339.13, 250/343
See application file for complete search history.

(56) References Cited

U.S. PATENT DOCUMENTS

| | | | |
|---|---|---|---|
| 3,995,960 A * | 12/1976 | Fletcher et al. | 356/433 |
| 5,173,749 A * | 12/1992 | Tell et al. | 356/437 |
| 5,317,156 A | 5/1994 | Cooper et al. | |
| 5,572,031 A * | 11/1996 | Cooper et al. | 250/343 |
| 6,008,928 A * | 12/1999 | Sachse et al. | 359/246 |
| 6,061,141 A | 5/2000 | Goldenberg et al. | |
| 6,064,488 A * | 5/2000 | Brand et al. | 356/440 |
| 7,576,538 B2 | 8/2009 | Meersmann et al. | |

OTHER PUBLICATIONS

McManus et al., "A high precision pulsed quantum cascade laser spectrometer for measurements of stable isotopes of carbon dioxide," Journal of Modern Optics, vol. 52, No. 16 (Nov. 2005) pp. 2309-2321.

Weidmann et al., "Development of a compact quantum cascade laser spectrometer for field measurements of CO2 isotopes," Appl. Phys. B, vol. 80 (Sep. 2004) pp. 255-260.

Tuzson et al., "Novel quantum-cascade laser based spectrometer for high precision isotopic ratio measurements of atmospheric CO2," Geophysical Research Abstracts, vol. 9 (Apr. 2007) 05398.

Notification of Transmittal of the International Search Report and the Written Opinion of the International Searching Authority, or the Declaration issued on Jul. 28, 2009 for corresponding International Application PCT/US09/41669 filed on Apr. 24, 2009 (8 pages).

* cited by examiner

*Primary Examiner* — Tarifur Chowdhury
*Assistant Examiner* — Isiaka Akanbi
(74) *Attorney, Agent, or Firm* — Samuel L. Borkowsky

(57) ABSTRACT

Gas having stable isotopes is monitored continuously by using a system that sends a modulated laser beam to the gas and collects and transmits the light not absorbed by the gas to a detector. Gas from geological storage, or from the atmosphere can be monitored continuously without collecting samples and transporting them to a lab.

15 Claims, 9 Drawing Sheets

APPARATUS AND METHOD FOR MONITORING OF GAS HAVING STABLE ISOTOPES

RELATED APPLICATIONS

This application claims the benefit of U.S. Provisional Patent Application Ser. No. 61/126,299 entitled "Detection of Gaseous Stable Isotopes," filed May 2, 2008, hereby incorporated by reference.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to an apparatus and method employing frequency-modulated spectroscopy for monitoring the stable isotopes in various gases.

BACKGROUND OF THE INVENTION

Some gaseous molecules ($CO_2$, $CH_4$, $O_3$, $N_2O$, chlorofluorocarbons) are known to cause climate change and increase pollution ($NO_x$, $O_3$, $SO_2$, $H_2S$) in the atmosphere. Measuring the stable isotopes of these gases can provide information about their origin, can differentiate these gases in various settings (e.g. $CH_4$ produced from a wetland or a pipeline leak), and can help track them through production/processing scenarios or through biological and/or chemical and/or physical pathways.

Determining ratios of stable isotopes of $CO_2$ ($^{12}CO_2$, $^{13}CO_2$) and other greenhouse gases (methane ($CH_4$), nitrous oxide ($N_2O$), for example) is used for determining the source(s) of these gases. A challenge with measuring stable isotope ratios is measuring the minor isotopic species because the minor species may be present in very small amounts. The natural abundance of $^{13}CO_2$ in atmospheric $CO_2$, for example, is only approximately 1.1%; the rest is $^{12}CO_2$. FIG. 1 shows ranges in isotopic variation of $CO_2$ from sources including natural gas, plants and microbes, air, magmatic sources, petroleum, and groundwater.

Current measurements of $\delta^{13}C$ (i.e. the carbon isotope ratio of $^{13}C/^{12}C$ within the $CO_2$ of an unknown sample relative to a standard which is a limestone from the PeeDee formation (PDB)) involves collecting samples at the site and delivering them to the laboratory where they are analyzed using by optical spectroscopy using a commercially available absorption instrument, or by mass spectrometry with a highly precise sector mass spectrometer. The optical approach suffers from the limitations of any approach associated with collecting samples, including the lack of in situ detection. The optical approach also requires high electrical power and a continuous source of cryogens, and is thus severely limited by its continuous user interface and maintenance requirements.

Detecting $CO_2$ seepage from a geologic storage system is difficult to do using $CO_2$ concentration alone. Typically, other trace gases like $CH_4$, inert tracers like perfluorocarbons, or natural tracers like the isotopes of $CO_2$ ($^{13}C/^{12}C$ and $^{14}C/^{12}C$ ratios) are used to identify $CO_2$ leaks at the ground surface. Current efforts focusing on stable isotope identification of $CO_2$ seepage has focused on point measurements using traps that limit both the temporal and spatial resolution of the leak.

Efforts have been made in creating systems that can be used in the field to conduct real time isotope measurements at a higher temporal frequency. Systems that can resolve isotopes over 5 to 15 minute windows of time are usually bulky, expensive, and not portable.

Stable isotopes (e.g. $^{13}C$) are important for monitoring carbon sequestration potential in geologic $CO_2$ storage systems. Point source measurements are all that can be made at this time, but remote-sensing tools that will provide spatial analysis of $CO_2$ sources is what is needed. Furthermore, there is a need for a technology that can also provide information about where the $CO_2$ came from.

An object of the invention is a portable system and method for continuously monitoring stable isotopes of gas.

Another object of the invention is a portable system and method for continuously monitoring $CO_2$.

Another object of the invention is a system and method for making in-situ measurements of stable isotopes of various gases.

Another object of the invention is a system and method for making remote measurements of stable isotopes.

Another object of the invention is a system and method for making real time measurement of stable isotopes of atmospheric gases.

SUMMARY OF THE INVENTION

In accordance with the purposes of the present invention, as embodied and broadly described herein, the present invention includes a system for monitoring stable isotopes of gas. The system includes a cell for receiving a sample of gas, a tunable diode laser for providing a laser beam having an original carrier frequency ($\omega_c$), and a modulation source operating in the radiofrequency regime for modulating the original carrier frequency ($\omega_c$) of the laser beam from the tunable diode laser, thereby producing a modulated laser beam having the original carrier frequency ($\omega_c$) and sidebands on either side of and evenly spaced apart from the carrier frequency by a modulation frequency ($\omega_m$). The sample of gas inside the multipass cell absorbs energy from the modulated laser beam. The system also includes a detector that provides a detection signal for a stable isotope from the gas sample inside the cell. The detector includes a reference channel and a signal channel. The system also includes an amplifier for amplifying the detection signal from the detector. An optical fiber transmits light from the cell to the signal channel of the detector. A focusing means such as a lens focuses the light from multipass cell into the optical fiber. A beamsplitter directs the modulated laser beam alternately between the cell and the reference channel of the detector.

The invention also includes a method for continuous in-situ monitoring of gas having stable isotopes. The method involves directing a frequency modulated laser beam alternately between a reference channel of a detector and a cell containing a first sample of a gas having stable isotopes. The gas interacts with the modulated laser beam and produces a light emission resulting from the interaction. The light emission is collected and transmitted through an optical fiber to a signal channel of the detector. Afterward, the first sample is replaced with a second sample of gas and the steps are repeated and the results compared. This allows continuous gas monitoring without having to collect samples and send them out to a laboratory for analysis.

The invention also includes a spectroscopic system for monitoring gas having stable isotopes. The system includes a tunable diode laser for providing a laser beam having an original carrier frequency ($\omega_c$). The system also includes a modulation source, either direct laser modulation or through an electro optical phase modulator, operating in the radiofrequency regime for modulating the original carrier frequency ($\omega_c$) of the laser beam from the tunable diode laser. The laser produces a modulated laser beam having the original carrier frequency ($\omega_c$) and sidebands on either side of and evenly spaced apart from the carrier frequency by a modulation frequency ($\omega_m$). Gas from the sample absorbs energy from the modulated laser beam. The system also includes a detector that provides a detection signal that can be used to differentiate stable isotopes from a gas sample. The detector includes a reference channel and a signal channel. The system also includes an amplifier for amplifying the detection signal from said detector. An optical fiber transmits light from the gas sample to the signal channel of said detector. A focusing means such as a collection lens collects light from the gaseous sample and focuses it into the optical fiber. A beamsplitter directs the modulated laser beam alternately between the reference channel of the detector and the gaseous sample.

The invention also includes a method for continuously monitoring $CO_2$. The method involves (a) directing a frequency modulated laser beam from a tunable diode laser simultaneously between a reference channel of a detector and gas remote from the detector, the gas comprising $CO_2$ that interacts with the modulated laser beam, whereby the gas absorbs energy from the modulated laser beam, (b) collecting the not absorbed by the gas, (c) transmitting the collected light through an optical fiber to a signal channel of the detector, (d) analyzing the transmission of collected light to provide a first $^{13}C/^{12}C$ ratio, (d) repeating steps (a), (b), (c), and (d) at a later time, thereby providing a second $^{13}C/^{12}C$ ratio for the gas, and (e) comparing first $^{13}C/^{12}C$ ratio with the second $^{13}C/^{12}C$ ratio, thereby monitoring the $CO_2$ as time passes. This method can be used to analyze gas from a geologic storage system that is remote from the detector. The method can also be used to monitor gas in the atmosphere. For atmospheric gas, the light collection step may involve reflecting light from an airborne platform in the atmosphere to a collector remote from the atmosphere. A mirror on an airplane might be used for the light reflection; thus the monitoring while the gas is in the atmosphere.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings:

FIG. 2b shows an actual spectrum with sidebands that result from frequency modulation.

FIG. 4a shows a $^{12}C^{16}O_2$ FM spectra collected with the remote instrument with a 20 m standoff. FIG. 4b shows $^{13}C^{16}O_2$ FM spectra collected with the remote instrument with a 20 m standoff. FIG. 4c shows $^{12}C^{16}O_2$ FM spectra collected with the in situ instrument. FIG. 4d shows $^{13}C^{16}O_2$ FM spectra collected with the in situ instrument.

DETAILED DESCRIPTION

The invention includes a system that optically monitors gaseous stable isotopes. The system employs frequency-modulated spectroscopy ("FMS"), which is a type of spectroscopy with a sensitivity that is orders of magnitude more sensitive than standard absorption spectroscopy.

Figure 2A:
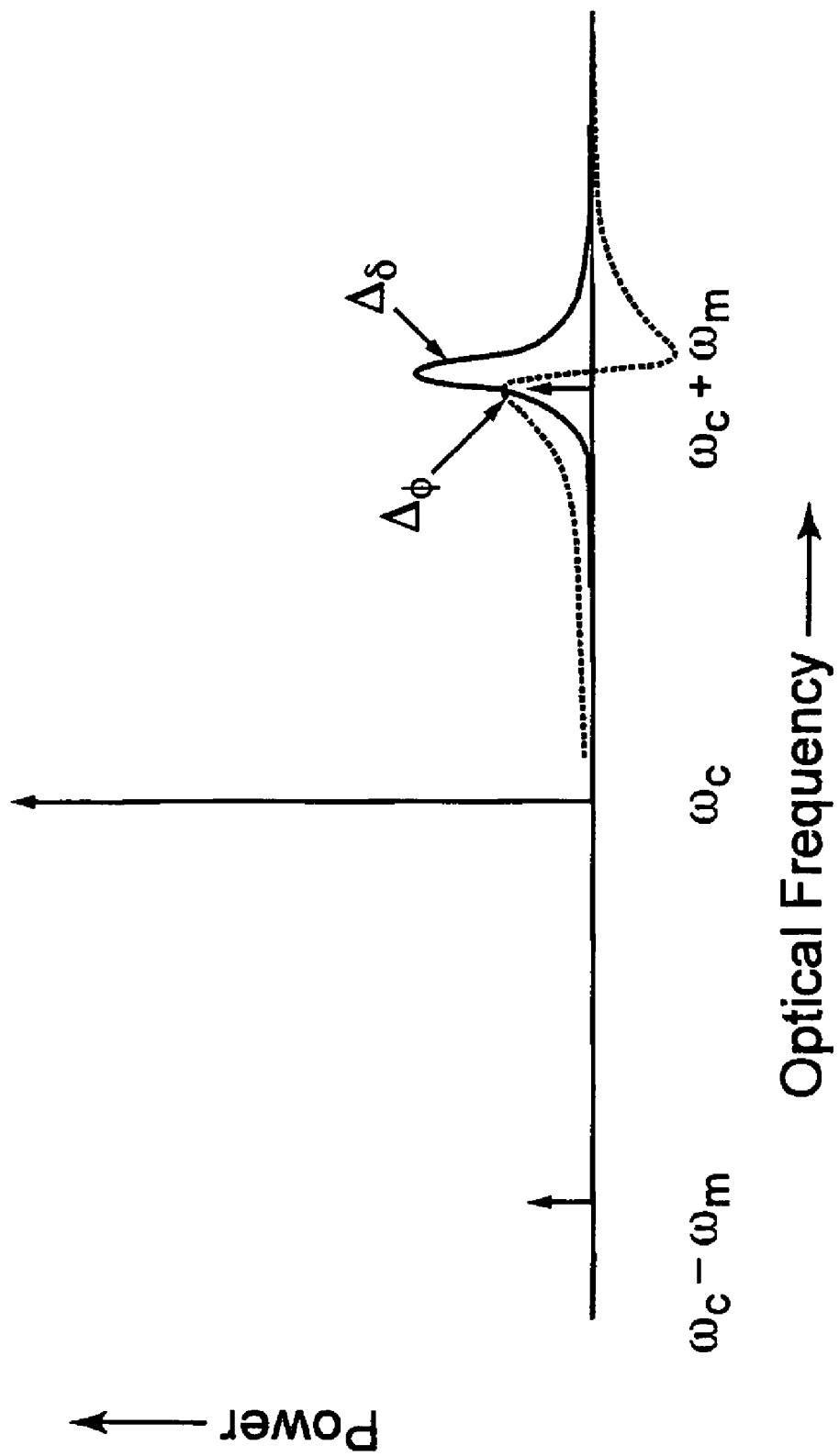
FIG. 2a-b shows plots that illustrate the effect of modulating the original carrier frequency of a tunable diode laser with an electro-optical phase modulator operating in the radiofrequency regime. The plot shown in FIG. 2a is a generic plot showing the original carrier frequency ($\omega_c$) of the beam from a tunable diode laser ("TDL"), along with sidebands ($\omega_c \pm \omega_m$) evenly spaced about the original carrier frequency ($\omega_c$) by the modulation frequency ($\omega_m$).
Figure 2B:
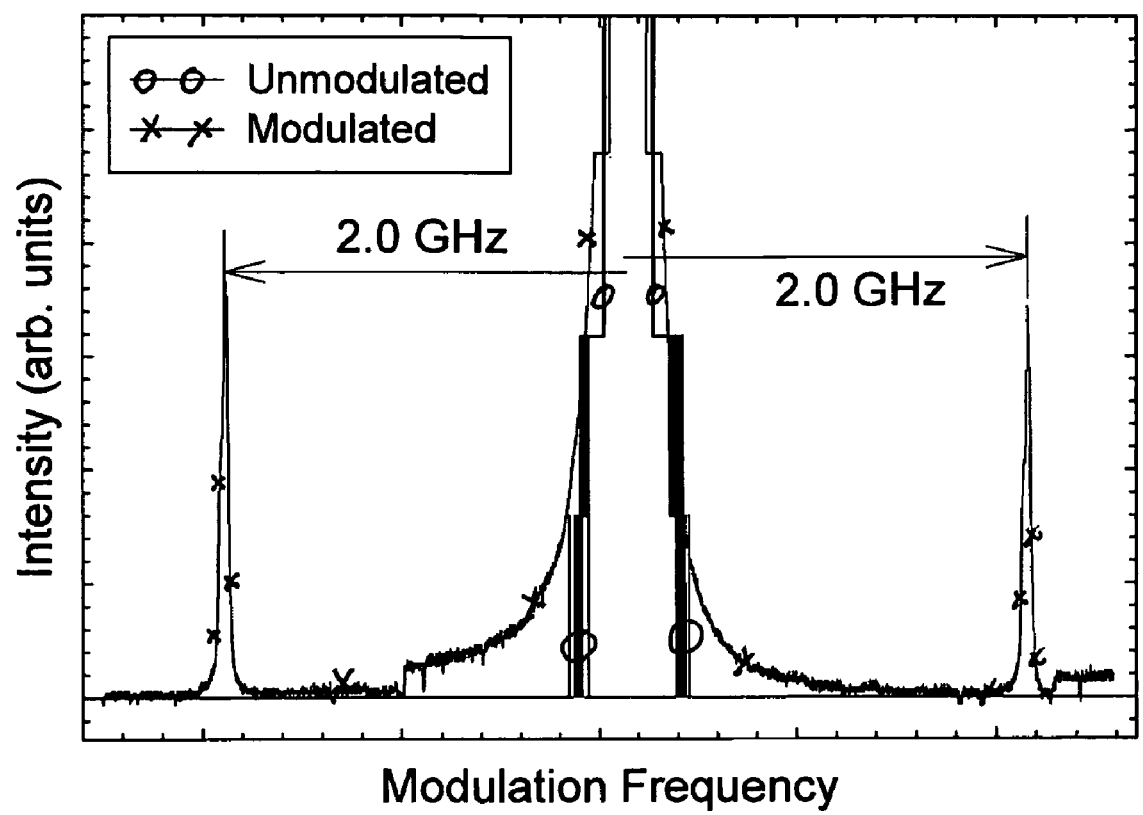

An embodiment system of the invention includes a tunable diode laser ("TDL") and an electro-optical phase modulator operating in the radiofrequency regime that modulates the laser beam from the tunable diode laser. The modulated laser beam has a frequency equal to that of the original carrier frequency ($\omega_c$) of the beam from the TDL, along with sidebands ($\omega_c \pm \omega_m$) evenly spaced about the original carrier frequency ($\omega_c$) by the modulation frequency ($\omega_m$), as depicted in FIG. 2. This modulation of the original carrier frequency is analogous to a modulation of a carrier frequency from a radio station. The carrier frequency is the radio station that one tunes to, and the audio is the modulated frequency. A species of interest is detected by tuning the TDL and the modulation frequency such that one of the sidebands interacts with a specific spectral feature. Turning to FIG. 2a, the Lorentzian shaped spectral feature $\Delta\delta$ is probed by the right sideband ($\omega_c + \omega_m$). One records the derivative shaped dotted line ($\Delta\phi$) as the carrier and modulated frequency is tuned over the spectral feature. By using a detection frequency in the radiofrequency regime, the laser noise is low, thus improving the signal to noise ratio. The greatly enhanced signal to noise ratio is important for improving detection limits of both major and minor isotopes.

Figure 3A:
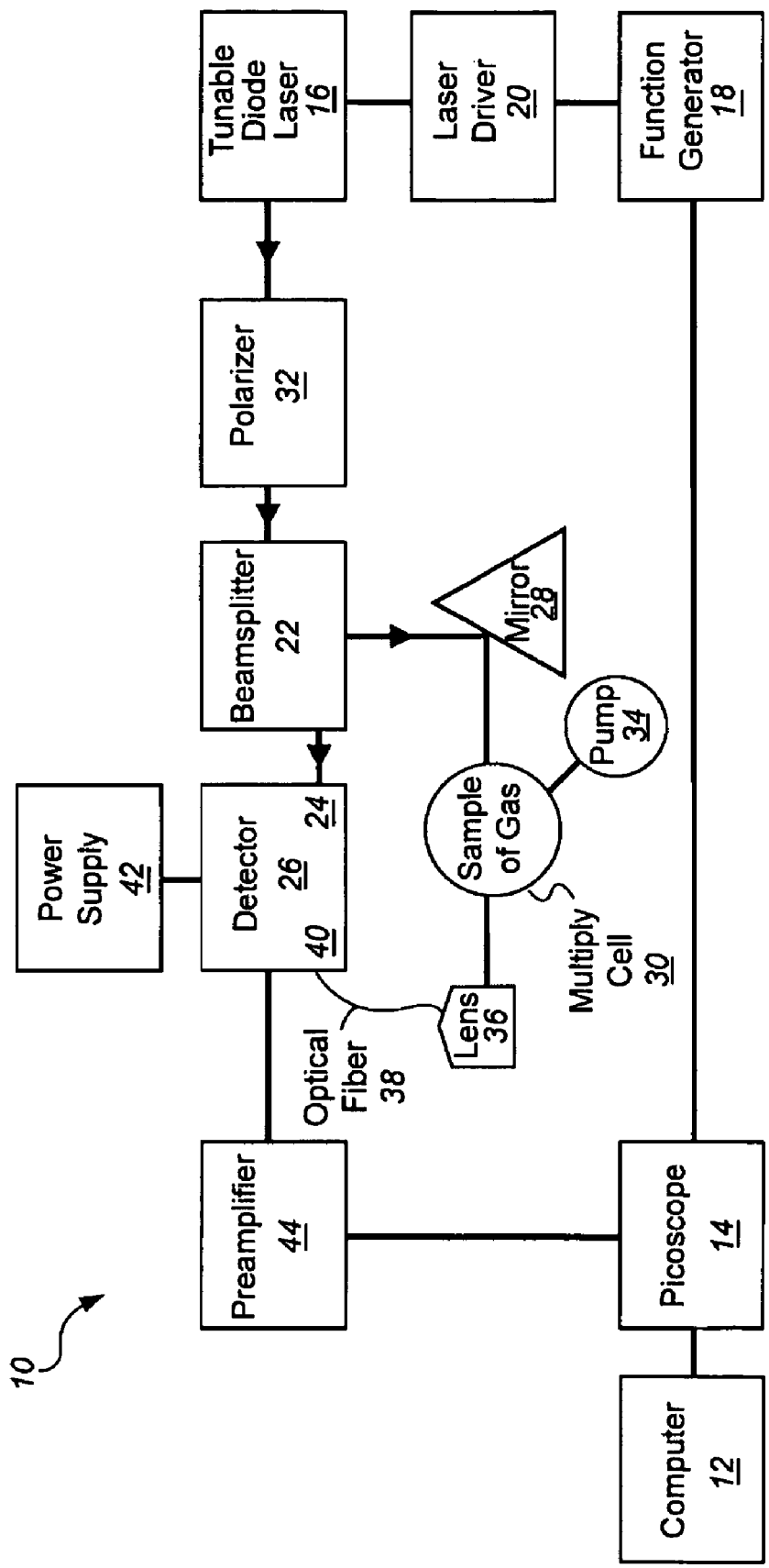
FIGS. 3a and 3b are schematic block diagrams of two embodiments of the apparatus of the present invention
Figure 3B:
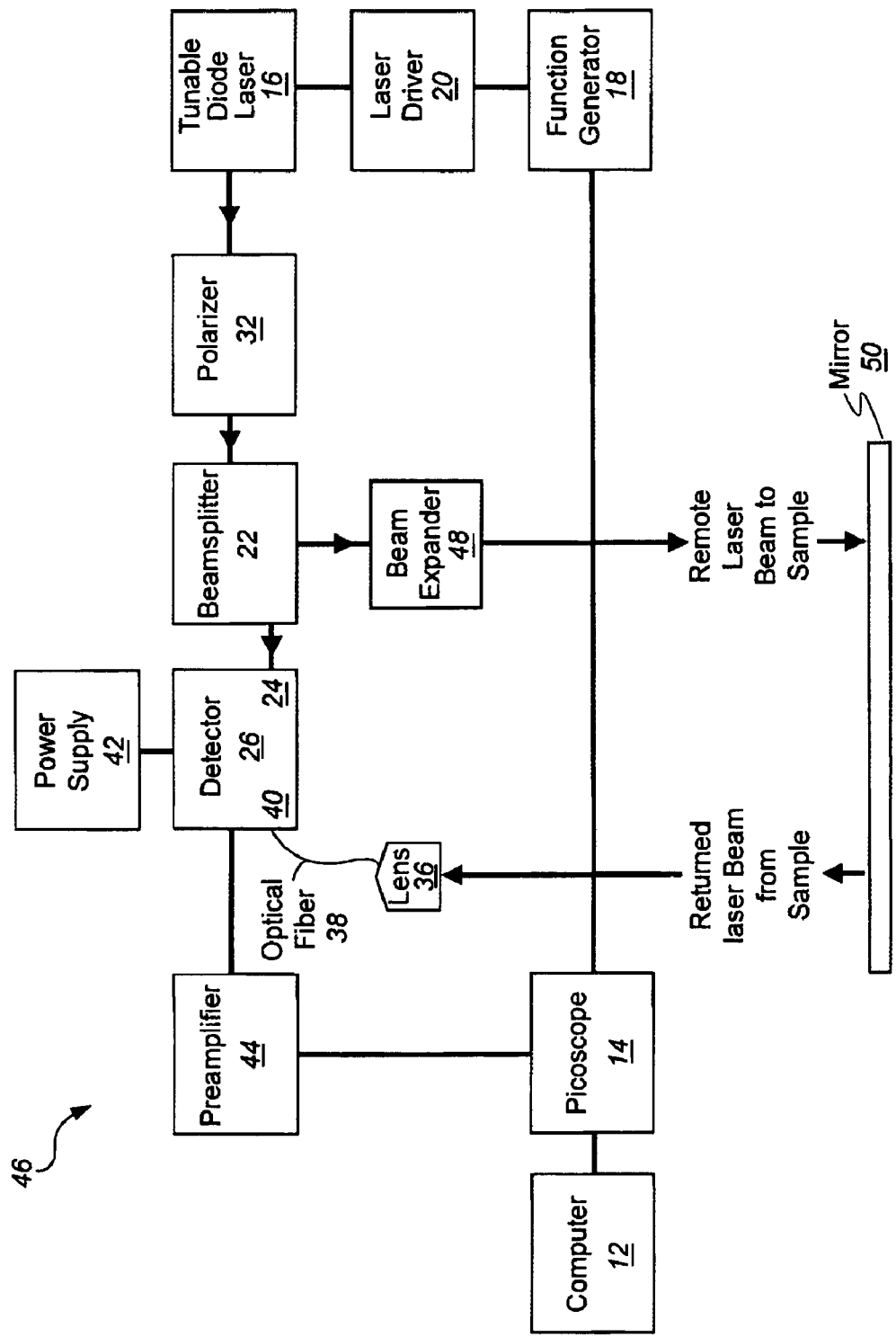

FIG. 3a and FIG. 3b show schematic block diagrams of two embodiments of the invention apparatus. FIG. 3a shows an embodiment apparatus for making in situ (i.e. closed path) measurements. FIG. 3b shows an embodiment for making remote (i.e. open path) measurements.

Turning first to FIG. 3a, a schematic block diagram of an embodiment apparatus 10 for making in situ (i.e. closed path) measurements of stable isotopes is shown. Apparatus 10 is driven by a computer 12. Apparatus 10 includes picoscope 14, which is a commercially-available oscilloscope used to record the data. Apparatus 10 includes diode laser 16 (NEW FOCUS velocity tunable diode laser TLB-6330H, for example) and function generator 18 (SRS DS 345 function generator, for example) that drives the modulation of a laser beam from laser 16 through a laser driver 20 (NEW FOCUS velocity laser driver TLB-6330-LN, for example). Function generator 18 generates a sine wave for laser driver 20 that generates the modulation frequency. Function generator 18 also triggers picoscope 14. Beamsplitter 22 (e.g. a beamsplitter cube) splits the modulated laser beam into a reference beam and a signal beam. The reference beam is sent directly to a reference channel 24 of a detector 26 (NEW FOCUS model 2017 Auto-balanced Receiver, for example). The signal beam is deflected by a mirror 28 to a multipass cell 30 (a 10 meter "White Cell," for example) containing a sample of gas. In an embodiment, a polarizer 32 permits adjustment of the fraction of modulated laser light directed to the gas sample in the multipass cell and reference channel via the beamsplitter. In an embodiment, a pump 34 provides the means for pumping a sample of gas into the multipass cell. The modulated laser beam interacts with gas inside multipass cell 30, and changes in the modulation sidebands are detected. Light emerging from multipass cell 30 is collected by lens 36 and focused into an optical fiber 38, which transmits the collected light to signal channel 40 of detector 26. Collection lens 36 can also act as a mount for optical fiber 38. A power supply 42 (NEW FOCUS 3211 15V, for example) provides power to detector 26. Preamplifier 44 (SRS SR 560 Low Noise Voltage Preamplifier, for example) amplifies the signal received by detector 26.

A Remote FMS embodiment apparatus 46 is shown in FIG. 3b. Remote (i.e. open path) apparatus 46 is similar to the in situ instrument 10 of FIG. 3a. Apparatus 46 also includes computer 12, picoscope 14, laser 16, function generator 18, laser driver 20, beamsplitter 22, detector 26 with reference channel 24 and signal channel 40, collection lens 36, optical fiber 38, power supply 42, and preamplifier 44, all configured the same way as for in situ embodiment apparatus 10. Apparatus 46, however, does not include a multipass cell for the gas sample. Instead, the modulated signal beam created by beamsplitter 22 is directed to a beam expander 48 that controls the beam divergence as it probes samples remotely. As the modulated beam exits beam expander, it interacts with a remote sample of gas. A remote mirror 50 reflects the light back to the FMS instrumentation. The returned laser light is collected and focused through collection lens 36 to optical fiber 38, which transmits the collected light to signal channel 40 of detector 26 just as described for the in situ embodiment apparatus 10. Power supply 42 provides power to detector 26, and a low noise voltage preamplifier 44 amplifies the signal.

Apparatus 46 has been used for remotely monitoring stable isotopes of $CO_2$ wherein the modulated laser beam interacts with $CO_2$ and changes in the modulation sidebands are detected. It could also be used for monitoring other atmospheric gases besides $CO_2$. An embodiment apparatus was constructed in the form of a tower on the ground in a field. A laser on the tower was directed up from the base of the tower to a mirror that directed the frequency modulated laser pulse to a detector. The laser could also be directed to another tower, which allows monitoring a region between the two towers.

Another embodiment of the invention employs an airborne platform (i.e. this embodiment is on an airplane) and may be used for regional monitoring of atmospheric gases ($CO_2$, for example). In this embodiment, the frequency-modulated laser beam is directed to a mirror (or other reflective surface) on a wing of the airplane. This embodiment apparatus can monitor $\delta^{13}C$ as the airplane flies over a region of interest.

Figure 1:
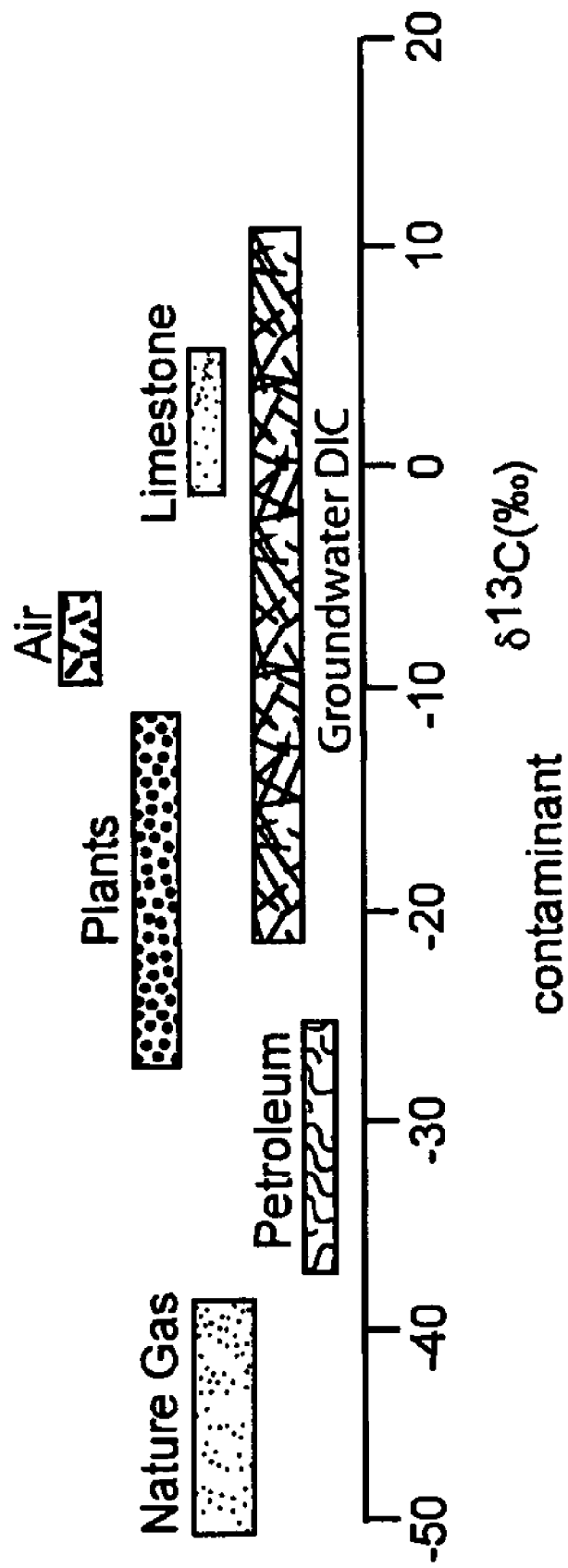
FIG. 1 is a graphical depiction of ranges in isotopic variation of $CO_2$ from sources including natural gas, plants and microbes, air, magmatic sources, petroleum, and groundwater.

An aspect of the invention is involved with carbon sequestration, in particular with monitoring $CO_2$ leaks and leak rates from geologic carbon storage sites. In this aspect of the invention, continuous, column averaged, spatially integrated measurements of $\delta^{13}CO_2$ were made using the apparatus 10 shown in FIG. 3a and the measurements are analyzed. Natural gas was pumped into an underground pipe to simulate a storage reservoir. Natural sources of $CO_2$ (e.g. plants and microbes, see FIG. 1) were distinguished from $CO_2$ released from underground pipe by using the $\delta^{13}C$ signature of the $CO_2$. Alternatively, natural gas could also be pumped into an underground aquifer or oil field so the method of the invention could be used to detect leakage from such an aquifer or oil field.

In another aspect of the invention, an embodiment apparatus can be used for monitoring leaks in a wellbore by fiber-optically coupling the laser to a probe that is lowered into the well.

There are other atmospheric gases besides carbon dioxide that have an impact on the changing climate. Some of these include methane, carbon monoxide, nitrous oxide, hydrogen sulfide, nitrogen oxides, and sulfur oxides ($SO_x$). An embodiment apparatus of the invention can be used to measure stable isotope ratios of atoms (e.g. $^{32}S$, $^{33}S$, $^{34}S$, $^{14}N$, $^{15}N$, $^{16}O$, $^{17}O$, $^{18}O$, $^{1}H$, $^{2}H$) of these other gaseous molecules. An embodiment apparatus has resolution sufficient for rotationally resolved spectra and therefore can be used to probe small molecules like CO or $N_2O$ or small highly symmetric molecules such as $CH_4$ and $SF_6$. Thus, an embodiment apparatus can provide information from these other atmospheric species about the impact they may have on climate change. The stable isotopes of carbon in $CO_2$ and $CH_4$ have been researched over the past 50 or so years, yet the isotope variation in nitrogen and sulfur in the climate change gases is a relatively new field. Any effort to extend FMS to these other climate changing species would require an investigation into better interpretation of the isotope ratios of nitrogen and sulfur. This would involve extracting samples from specific sources from which one can correlate the relationship between source of the species and the stable isotope ratio.

Figure 4A:
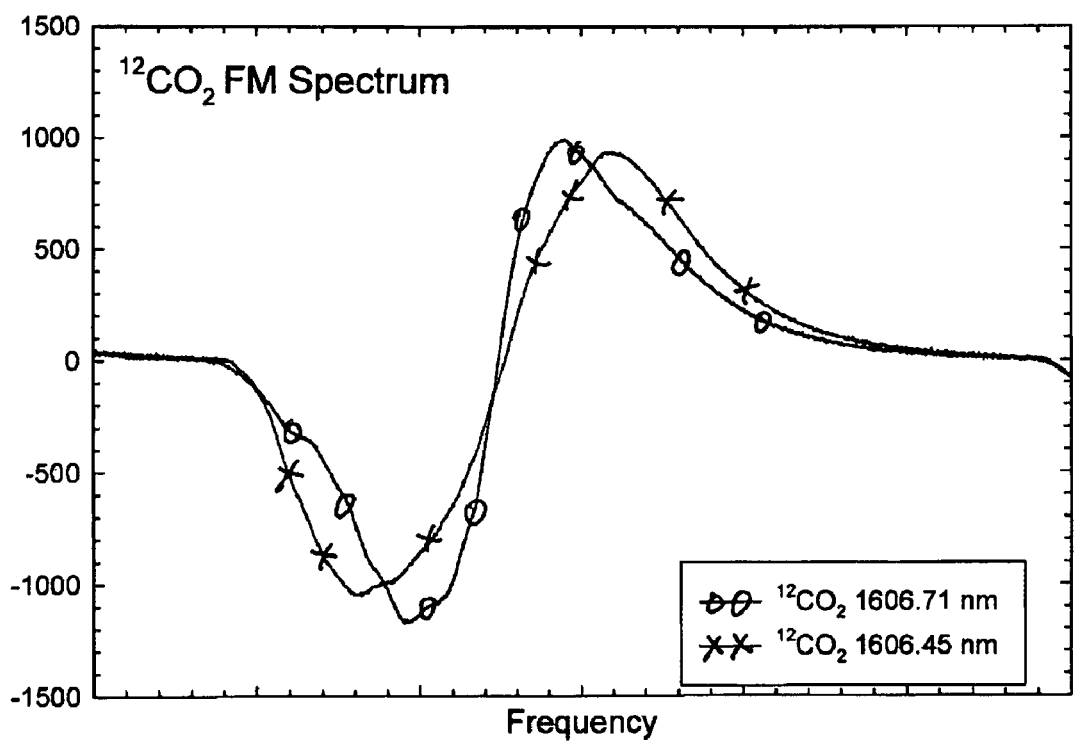
FIG. 4a-d shows a variety of spectra obtained using an embodiment system of this invention.
Figure 4B:
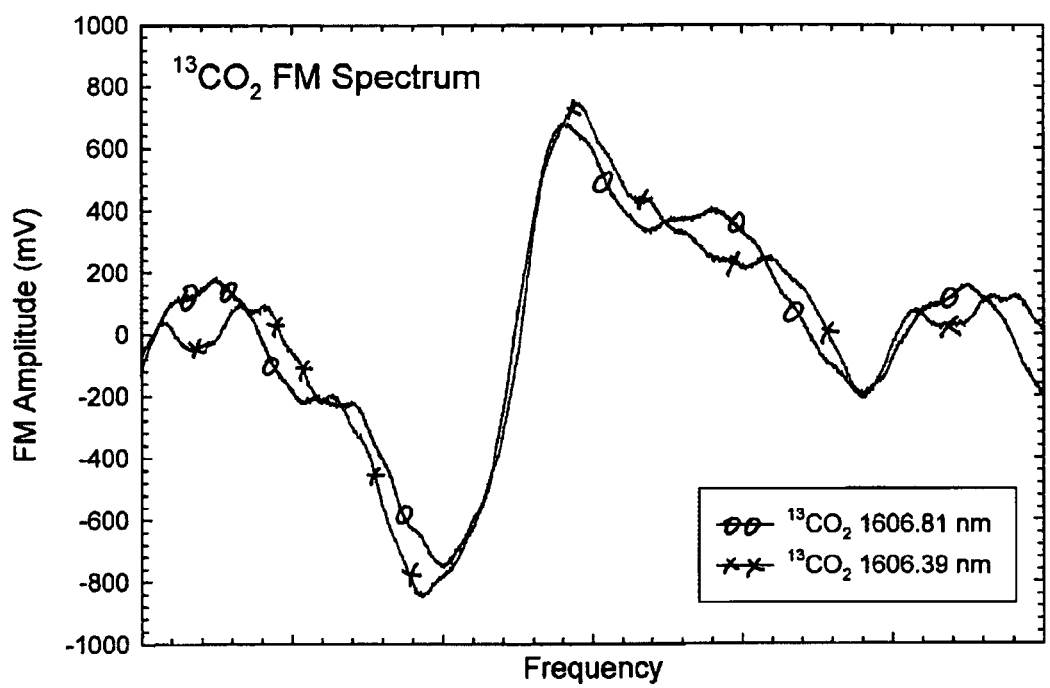
Figure 4C:
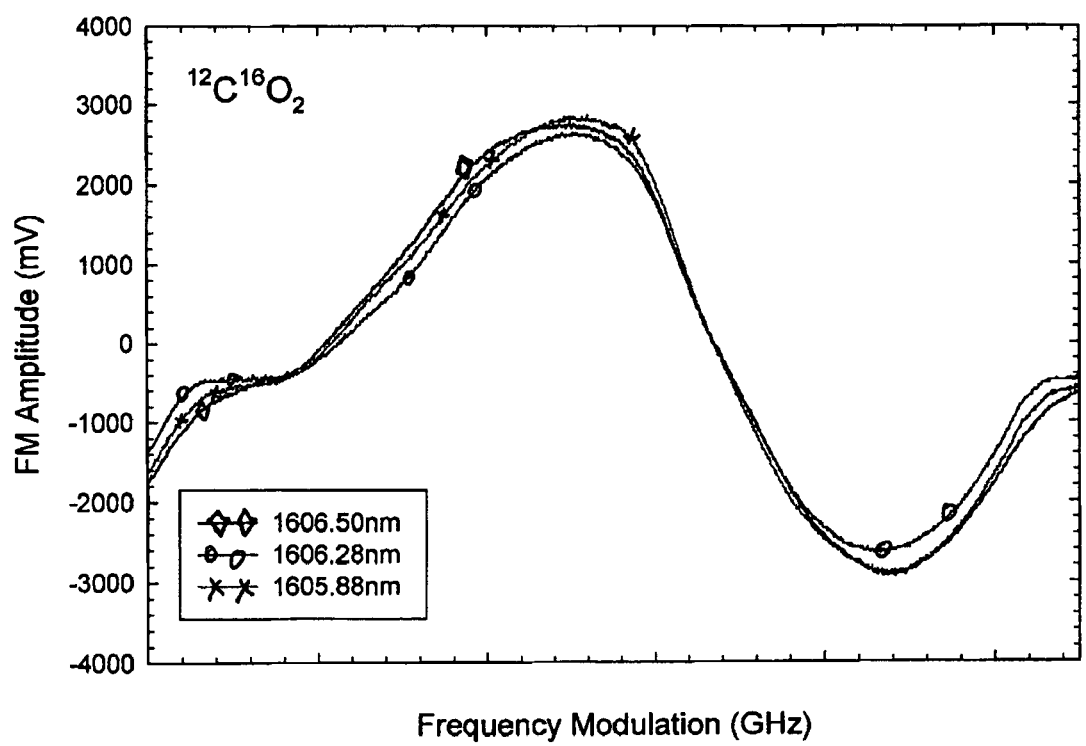
Figure 4D:
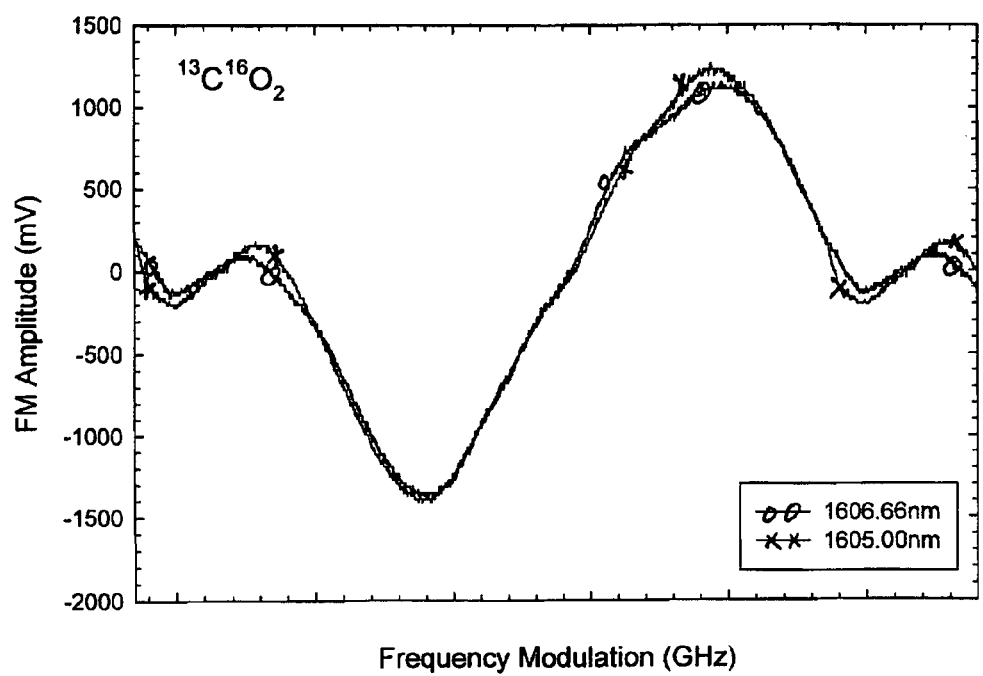

The FMS experiment involves tuning the laser such that one of the sidebands in FIG. 2 is absorbed by the species of interest. Ideally, the carrier ($\omega_c$) and sidebands ($\omega_c \pm \omega_m$) are not absorbed by any other absorption features. The detector is sensitive to the relative changes between the sidebands. For $^{12}C^{16}O_2$ and $^{13}C^{16}O_2$, this instrument monitors many of the absorption features in the 1595-1614 nm spectral region where the stable isotopes can be resolved. The peak-to-peak intensity is proportional to the concentration of $CO_2$ in the sample. FIG. 4a-d shows a variety of spectra obtained using an embodiment system of this invention. FIG. 4a shows a $^{12}C^{16}O_2$ FM spectra collected with the remote instrument with a 20 meter standoff. FIG. 4b shows $^{13}C^{16}O_2$ FM spectra collected with the remote instrument with a 20 meter standoff. FIG. 4c shows $^{12}C^{16}O_2$ FM spectra collected with the in situ instrument. FIG. 4d shows $^{13}C^{16}O_2$ FM spectra collected with the in situ instrument. To obtain each of these spectra, the laser was tuned to the wavelength shown in the legend and one of the sidebands interacted with the absorption feature as depicted in FIG. 2, generating the FM spectra shown in the FIG. 4a-d.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A system for monitoring stable isotopes from a sample of gas comprising:
   a cell for receiving a sample of gas,
   a pump for sending the sample of gas into the cell,
   a tunable diode laser for providing a laser beam having an original carrier frequency ($\omega_c$),
   a modulation source operating in the radiofrequency regime for modulating the original carrier frequency ($\omega_c$) of the laser beam from the tunable diode laser, thereby producing a modulated laser beam having the original carrier frequency ($\omega_c$) and sidebands on either side of and evenly spaced apart from the carrier frequency by a modulation frequency ($\omega_m$), the modulated laser beam directed at a sample of gas inside the cell, a detector for providing a detection signal from a stable isotope from the gas sample inside the cell, said detector comprising a reference channel and a signal channel, an amplifier for amplifying the detection signal from said detector, an optical fiber for transmitting light from the multipass cell to the signal channel of said detector, a focusing means for focusing light from the cell into the optical fiber, a beamsplitter for directing the modulated laser beam simultaneously to the cell and to the reference channel of the detector, and a polarizer for adjusting fractions of modulated laser light directed to the cell and the reference channel of the detector via the beamsplitter, wherein the system lacks a reference cell and is configured such that said beamsplitter splits the modulated laser beam into a reference beam and a signal beam, wherein said reference beam is sent directly to the reference channel of the detector and said signal beam is sent to said cell containing a sample of gas and afterward to the signal channel of the detector.

2. The system of claim 1, wherein said cell for receiving a gas sample is a multipass cell.

3. The system of claim 1, wherein said modulation source is capable of direct laser modulation.

4. The system of claim 1, wherein said modulation source comprises an electro optical phase modulator.

5. A method for continuously monitoring a gas comprising stable isotopes, comprising:

pumping a first sample of gas having stable isotopes into a cell, splitting a frequency modulated laser beam into a reference beam and a signal beam, directing the reference beam directly to a reference channel of a detector while simultaneously directing the signal beam to a cell containing the first sample of a gas having stable isotopes, the gas interacting with the signal beam and producing a first light emission from the interaction, transmitting the first light emission through an optical fiber to a signal channel of the detector, replacing the first sample of the gas with a second sample of a gas pumped into the cell, the second sample of gas producing a second light emission, transmitting the second light emission through the optical fiber to the signal channel of the detector, comparing the first light emission with the second light emission, thereby continuously monitoring the gas.

6. The method of claim 5, wherein the first and second samples of the gas are taken from approximately the same location so that changes in gas composition from that location are monitored as time passes.

7. The method of claim 6, further comprising repeating the steps of the method at a different location so that changes in gas composition at different locations are monitored and may be compared as time passes.

8. The method of claim 5, wherein the gas is $CO_2$.

9. A spectroscopic system for regional monitoring of atmospheric gas comprising:

a tunable diode laser for providing a laser beam having an original carrier frequency ($\omega_c$), a modulation source operating in the radiofrequency regime for modulating the original carrier frequency ($\omega_c$) of the laser beam from the tunable diode laser, thereby producing a modulated laser beam having the original carrier frequency ($\omega_c$) and sidebands on either side of and evenly spaced apart from the carrier frequency by a modulation frequency ($\omega_m$), the modulated laser beam directed at a sample of gas, a detector for providing a detection signal from a stable isotope from a gas sample comprising stable isotopes, said detector comprising a reference channel and a signal channel, an amplifier for amplifying the detection signal from said detector, an optical fiber for transmitting light from the gas sample to the signal channel of said detector, a focusing means for focusing light emitted from the gaseous sample into the optical fiber, a beamsplitter for splitting the modulated laser beam into a reference beam and a signal beam, the system lacking a reference cell and configured such that the reference beam is sent directly to the reference channel of the detector and the signal beam is sent to a beam expander, a beam expander for controlling beam divergence as the signal beam probes a remote sample of gas, an airplane comprising an airplane wing having a mirror thereon for reflecting the light from the remote sample of gas as the airplane flies over a region of interest, a collection lens for receiving the light reflected from the mirror on the airplane wing, wherein said optical fiber transmits the collected light from the collection lens to the signal channel of said detector.

10. A method for continuously monitoring $CO_2$, comprising:

(a) splitting a frequency modulated laser beam from a tunable diode laser into a reference beam and a signal beam and simultaneously sending the signal beam to gas remote from the detector while sending the reference beam directly to a reference channel of the detector, the gas comprising $CO_2$ that interacts with the modulated laser beam, whereby the gas absorbs energy from the signal beam, (b) collecting the light not absorbed by the gas and (c) transmitting the collected light through an optical fiber to a signal channel of the detector, (d) analyzing the light transmission to provide a first $^{13}C/^{12}C$ ratio, (e) repeating steps (a), (b), (c), and (d) at a later time, thereby providing a second $^{13}C/^{12}C$ ratio, and (f) comparing first $^{13}C/^{12}C$ ratio with the second $^{13}C/^{12}C$ ratio, thereby monitoring $CO_2$ remotely in-situ as time passes.

11. The method of claim 10, wherein the sample of gas is from underground.

12. The method of claim 10, wherein the gas is in the atmosphere.

13. The method of claim 10, wherein the step of collecting the light not absorbed by the gas comprises reflecting collected light from an airborne platform in the atmosphere to a collection lens remote from the atmosphere.

14. The method of claim 10, wherein the modulation source is capable of direct laser modulation.

15. The method of claim 10, wherein the modulation source comprises an electro optical phase modulator.

* * * * *